(12) United States Patent
Silvestrini (10) Patent No.: US 10,076,140 B2
(45) Date of Patent: Sep. 18, 2018

(54) AEROSOL-GENERATING SYSTEM FOR DELIVERING NICOTINE SALT PARTICLES

(71) Applicant: Philip Morris Products S.A., Neuchatel (CH)

(72) Inventor: Patrick Charles Silvestrini, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 15/305,469

(22) PCT Filed: Jun. 23, 2015

(86) PCT No.: PCT/EP2015/064129
§ 371 (c)(1),
(2) Date: Oct. 20, 2016

(87) PCT Pub. No.: WO2015/197627
PCT Pub. Date: Dec. 30, 2015

(65) Prior Publication Data
US 2017/0095002 A1  Apr. 6, 2017

(30) Foreign Application Priority Data
Jun. 24, 2014 (EP) .................................... 14173788

(51) Int. Cl.
*A24F 47/00* (2006.01)
*H05B 1/02* (2006.01)
(52) U.S. Cl.
CPC ......... *A24F 47/008* (2013.01); *H05B 1/0244* (2013.01); *H05B 2203/021* (2013.01)

(58) Field of Classification Search
CPC ..................................................... A24F 47/008
(Continued)

(56) References Cited

U.S. PATENT DOCUMENTS 8,381,739 B2    2/2013  Gonda
9,516,899 B2 *  12/2016 Plojoux ................. A24F 47/002
(Continued)

FOREIGN PATENT DOCUMENTS

EA      200601250 A1   12/2006
JP      2007-512880 A   5/2007
(Continued)

OTHER PUBLICATIONS

Office Action dated Jul. 10, 2017 in Japanese Patent Application No. 2016-574927 (with English language translation).
(Continued)

*Primary Examiner* — Phuong Dinh
(74) *Attorney, Agent, or Firm* — Oblon, McClelland, Maier & Neustadt, L.L.P.

(57) ABSTRACT

An aerosol-generating system is provided, including a nicotine source, a lactic acid source, and a single heater configured to heat both the nicotine source and the lactic acid source. The aerosol-generating system may also include an aerosol-generating article including a cartridge having a first compartment including the nicotine source and a second compartment including the lactic acid source; and an aerosol-generating device including the single heater. The cartridge may also include a cavity configured to receive the single heater of the aerosol-generating device.

15 Claims, 3 Drawing Sheets

(58) Field of Classification Search
USPC .................. 131/173–280, 328, 329
See application file for complete search history.

(56) References Cited

U.S. PATENT DOCUMENTS

| | | |
|---|---|---|
| 2005/0016549 A1 | 1/2005 | Banerjee et al. |
| 2012/0006342 A1 | 1/2012 | Rose et al. |
| 2013/0192615 A1 | 8/2013 | Tucker et al. |
| 2013/0192616 A1 | 8/2013 | Tucker et al. |
| 2013/0192619 A1 | 8/2013 | Tucker et al. |
| 2013/0192620 A1 | 8/2013 | Tucker et al. |
| 2013/0192621 A1 | 8/2013 | Li et al. |
| 2013/0192622 A1 | 8/2013 | Tucker et al. |
| 2013/0192623 A1 | 8/2013 | Tucker et al. |
| 2014/0060554 A1 | 3/2014 | Collett et al. |
| 2015/0282084 A1* | 10/2015 | Katori ............... H04W 52/0225 370/311 |
| 2015/0335071 A1* | 11/2015 | Brinkley .............. F22B 1/284 131/328 |
| 2016/0073695 A1* | 3/2016 | Sears .................. H05B 3/46 131/329 |

FOREIGN PATENT DOCUMENTS

| | | |
|---|---|---|
| JP | 2012-520736 A | 9/2012 |
| JP | 2015-513393 A | 5/2015 |
| KR | 10-0636287 B1 | 10/2006 |
| KR | 10-2011-0139238 A | 12/2011 |
| KR | 10-2012-0101654 A | 9/2012 |
| WO | WO 2008/121610 A1 | 10/2008 |
| WO | 2010/107613 A1 | 9/2010 |
| WO | WO 2013/098395 A1 | 7/2013 |
| WO | WO 2015/000974 A1 | 1/2015 |

OTHER PUBLICATIONS

"A Randomised Placebo-Controlled Trial of a Nicotine Inhaler and Nicotine Patches for Smoking Cessation" Online http://www.otago.ac.nz/wellington/otago047634, Sep. 27, 2013, 5 Pages.
International Search Report and Written Opinion dated Sep. 25, 2015 in PCT/EP2015/064129 filed Jun. 23, 2015.
Office Action dated Feb. 28, 2017 in European Patent Application No. 15 731 310.7.
Decision to Grant dated Mar. 19, 2018 in Japanese Patent Application No. 2016-574927 (with English language translation).
Office Action dated Aug. 31, 2017 in Korean Patent Application No. 10-2016-7034135 (with English language translation).
Office Action dated Mar. 27, 2018 in corresponding Korean Patent Application No. 10-2016-7034135 (with English Translation), 20 pages.
Decision to Grant with English translation dated May 30, 2018 in the corresponding Kazakhstan Patent Application No. 2017/0031.1, (8 pages).

* cited by examiner

AEROSOL-GENERATING SYSTEM FOR DELIVERING NICOTINE SALT PARTICLES

TECHNICAL FIELD

The present invention relates to an aerosol-generating system comprising a nicotine source and a lactic acid source for generating an aerosol comprising nicotine lactate salt particles. The present invention also relates to an aerosol-generating article comprising a nicotine source and a lactic acid source and an aerosol-generating device comprising a single heater for use in such an aerosol-generating system. The present invention further relates to a method of controlling the reaction stoichiometry between nicotine vapour and lactic acid vapour in an aerosol-generating system for the in situ generation of an aerosol comprising nicotine lactate acid salt particles.

DESCRIPTION OF THE RELATED ART

Devices for delivering nicotine to a user comprising a nicotine source and a delivery enhancing compound source are known. For example, WO 2008/121610 A1 discloses devices in which nicotine and a volatile acid, such as pyruvic acid, are reacted with one another in the gas phase to form an aerosol of nicotine salt particles that can be inhaled by a user.

Differences between the vapour concentrations of nicotine and the volatile delivery enhancing compound in such devices may disadvantageously lead to an unfavorable reaction stoichiometry or the delivery of excess reactant, such as unreacted nicotine vapour or unreacted volatile delivery enhancing compound vapour to a user. The vapour pressure of pyruvic acid at ambient temperature is substantially greater than that of nicotine. Consequently, to balance the concentration of pyruvic acid vapour and nicotine vapour to yield an efficient reaction stoichiometry, it may be necessary to heat the nicotine source and the pyruvic acid source of devices disclosed in WO 2008/121610 A1 to different temperatures. Specifically, it may be necessary to heat the nicotine source to a higher temperature than the pyruvic acid source in order to generate a sufficient or consistent quantity of nicotine pyruvate salt particles for delivery to a user. This requires the nicotine source and the pyruvic acid source to be stored and heated in physically separate cartridges or other components within the device. The need for differential heating of the nicotine source and pyruvic acid source may thereby disadvantageously increase the complexity and cost of manufacturing the device.

SUMMARY

It is an object of the present invention to provide an aerosol-generating system for the in situ generation of an aerosol comprising a nicotine salt having a simple heating mechanism. It is another object of the present invention to provide such an aerosol-generating system that enables an efficient reaction stoichiometry and consistent nicotine delivery to a user to be achieved.

According to the present invention there is provided an aerosol-generating system comprising: a nicotine source; a lactic acid source; and a single heater configured to heat both the nicotine source and the lactic acid source. Advantageously, the single heater is configured to heat the nicotine source and the lactic acid source to substantially the same temperature.

According to the present invention there is further provided a method of controlling the reaction stoichiometry between nicotine vapour and lactic acid vapour in an aerosol-generating system for the in situ generation of an aerosol comprising nicotine lactate acid salt particles, the method comprising controlling the ratio of the volumetric airflow through a first compartment comprising a nicotine source and a second compartment comprising a lactic acid source.

BRIEF DESCRIPTION OF THE DRAWINGS

Embodiments will now be further described, by way of example only, with reference to the accompanying drawings in which:

FIGS. 7(i)-(iv) show schematic longitudinal cross-sections of an aerosol-generating system according to a third embodiment during assembly thereof comprising a sixth embodiment of an aerosol-generating article.

DETAILED DESCRIPTION

As used herein with reference to the present invention, by "substantially the same temperature" it is meant that the difference in temperature of the nicotine source and the lactic acid source measured at corresponding locations relative to the single heater is less than about 3° C. Preferably, the single heater is configured to heat the nicotine source and the lactic acid source to the same temperature.

As used herein with reference to the present invention, by "in situ" it is meant that, in use, nicotine vapour released from the nicotine source and lactic acid vapour released from the lactic acid source react with one another in the gas phase within the aerosol-generating system according to the present invention to form an aerosol comprising nicotine lactate salt particles.

Preferably, the aerosol-generating system according to the present invention is a pulmonary delivery system for generating an aerosol comprising nicotine lactate salt particles that is inhalable into a user's lungs.

The aerosol-generating system according to the present invention may be a single-piece system. In such embodiments, the single-piece system comprising the nicotine source, the lactic acid source and the single heater is discarded after use.

Advantageously, the aerosol-generating system according to the present invention may be a multi-piece system comprising two or more pieces that are configured to engage and cooperate with one another to form an aerosol-generating system for the in situ generation of an aerosol comprising nicotine lactate salt particles. Preferably, the multi-piece system comprises two, three or four pieces. In such embodiments, the multi-piece system may comprise one or more consumable pieces that are discarded after use and one or more reusable pieces. For example, the multi-piece system may comprise a consumable piece comprising the nicotine source and the lactic acid source and a reusable piece comprising the single heater.

In such embodiments, the multi-piece system may comprise suitable connecting means, such as, for example, mechanical connecting means, to enable the two or more pieces thereof to be detachably connected to one another without adversely impacting the functionality of the system as compared to a single-piece system.

In preferred embodiments, the aerosol-generating system according to the present invention comprises an aerosol-generating article comprising the nicotine source and the lactic acid source; and an aerosol-generating device comprising the single heater. In such embodiments, the aerosol-generating article and the aerosol-generating device are configured to engage and cooperate with one another to form an aerosol-generating system for the in situ generation of an aerosol comprising nicotine lactate acid salt particles.

In particularly preferred embodiments, the aerosol-generating system according to the present invention comprises a consumable aerosol-generating article comprising the nicotine source and the lactic acid source; and a reusable aerosol-generating device comprising the single heater.

As used herein with reference to the present invention, the term "aerosol-generating device" refers to a device comprising a single heater that is configured to interact with an aerosol-generating article comprising a nicotine source and a lactic acid source to generate an aerosol comprising nicotine lactate salt particles.

As used herein with reference to the present invention, the term "aerosol-generating article" refers to an article comprising a nicotine source capable of releasing nicotine and a lactic acid source capable of releasing lactic acid, wherein the nicotine and lactic acid can react with one another in the gas phase to form an aerosol comprising nicotine lactate salt particles.

Generally, the aerosol-generating system according to the present invention may comprise a combination of any aerosol-generating article comprising a nicotine source and a lactic acid source and any aerosol-generating device comprising a single heater configured to heat both the nicotine source and the lactic acid source.

As further described and illustrated below, preferred is an aerosol-generating article comprising a cartridge comprising a first compartment comprising the nicotine source and a second compartment comprising the lactic acid source.

Particularly preferred is an aerosol-generating article comprising a cartridge comprising a first compartment comprising the nicotine source, a second compartment comprising the lactic acid source and a cavity for receiving the single heater of the aerosol-generating device. Preferred for use with such an aerosol-generating article is an aerosol-generating device comprising: a body portion comprising the single heater; and a mouthpiece portion configured for engagement with the body portion, wherein the aerosol-generating device is configured to receive the aerosol-generating article such that the single heater of the body portion is received in the cavity in the cartridge. In such embodiments, the aerosol-generating device may further comprise a guide portion configured for engagement with the body portion to facilitate proper alignment of the single heater with the cavity in the cartridge.

According to the present invention there is further provided an aerosol-generating article for use in an aerosol-generating system according to the invention comprising a cartridge, the cartridge comprising: a first compartment comprising a nicotine source; a second compartment comprising a lactic acid source; and a cavity for receiving a single heater configured to heat the nicotine source and the lactic acid source.

According to the present invention there is further provided an aerosol-generating device for use in an aerosol-generating system according to the invention comprising: a body portion comprising a single heater; and a mouthpiece portion configured for engagement with the body portion, wherein the aerosol-generating device is configured to receive an aerosol-generating article comprising a cartridge comprising a first compartment comprising a nicotine source, a second compartment comprising a lactic acid source and a cavity such that the single heater of the body portion is received in the cavity.

As used herein with reference to embodiments of the present invention, the terms "upstream", "downstream", "proximal" and "distal" are used to describe the relative positions of components, or portions of components, of the aerosol-generating system, the aerosol-generating article and the aerosol-generating device according to the present invention.

The aerosol-generating system according to the present invention comprises a proximal end through which, in use, an aerosol exits the aerosol-generating system for delivery to a user. The proximal end may also be referred to as the mouth end. In use, a user draws on the proximal end of the aerosol-generating system in order to inhale an aerosol generated by the aerosol-generating system. The aerosol-generating system comprises a distal end opposed to the proximal end.

When a user draws on the proximal end of the aerosol-generating system, air is drawn into the aerosol-generating system, passes through the aerosol-generating system and exits the aerosol-generating system at the proximal end. Components, or portions of components, of the aerosol-generating system may be described as being upstream or downstream of one another based on their relative positions between the proximal end and the distal end of the aerosol-generating system.

As used herein with reference to the present invention, the term "longitudinal" is used to describe the direction between the proximal end and the opposed distal end of the aerosol-generating system and the term "transverse" is used to describe the direction perpendicular to the longitudinal direction.

As used herein with reference to the present invention, by "length" is meant the maximum longitudinal dimension between the distal end and the proximal end of components, or portions of components, of the aerosol-generating system.

The vapour pressures of lactic acid and nicotine as function of temperature are similar. Inclusion of these two reactants having a similar volatility in the aerosol-generating system and the aerosol-generating article according to the present invention advantageously allows an efficient reaction stoichiometry to be achieved by heating the nicotine source and the lactic acid source to substantially the same temperature using a single heater. As described and illustrated further below, this enables the nicotine source and the lactic acid source to be stored and heated in two compartments in a single component within the aerosol-generating system and the aerosol-generating article according to the present invention. This advantageously reduces the complexity and cost of manufacturing the aerosol-generating system and the aerosol-generating article according to the present invention compared to prior art devices in which the nicotine source and the volatile delivery enhancing compound source are stored and heated in physically separate components within the device.

Heating the nicotine source and the lactic acid source to a temperature above ambient temperature using a single heater allows control of the amount of nicotine vapour and lactic acid vapour released from the nicotine source and the lactic acid source, respectively. This advantageously enables the vapour concentrations of the nicotine and the lactic acid to be controlled and balanced proportionally to yield an efficient reaction stoichiometry. This advantageously improves the efficiency of the formation of an aerosol and the consistency of nicotine delivery to a user. It also advantageously reduces the risk of undesired delivery of excess reactant, that is unreacted nicotine vapour or unreacted lactic acid vapour, to a user.

The aerosol-generating system and the aerosol-generating device according to the present invention comprise a single heater. This advantageously provides for a simple device construction.

The single heater is configured to heat both the nicotine source and the lactic acid source. In preferred embodiments, the single heater is configured to heat both the nicotine source and the lactic acid source to a temperature of below about 250 degrees Celsius (° C.). In particularly preferred embodiments, the single heater is configured to heat the nicotine source and the lactic acid source to substantially the same temperature of between about 80° C. and about 150° C.

Where the aerosol-generating system according to the present invention comprises an aerosol-generating article comprising the nicotine source and the lactic acid source and an aerosol-generating device comprising the single heater, the single heater may be configured as an external heater that in use is positioned externally to the aerosol-generating article. Alternatively, the single heater may be configured as an internal heater that in use is positioned internally to the aerosol-generating article.

Preferably, the single heater is configured as an internal heater.

Where the single heater is configured as an internal heater, the aerosol-generating device may advantageously comprise guide means to facilitate proper alignment of the internal heater with the aerosol-generating article.

The aerosol-generating system and the aerosol-generating device according to the present invention may further comprise a power supply for supplying power to the single heater and a controller configured to control a supply of power from the power supply to the single heater. Alternatively, the aerosol-generating system and the aerosol-generating device according to the present invention may comprise a controller configured to control a supply of power from an external power supply to the single heater.

The aerosol-generating system and the aerosol-generating device according to the present invention may further comprise one or more temperature sensors configured to sense the temperature of at least one of the single heater, the nicotine source and the lactic acid source. In such embodiments, the controller may be configured to control a supply of power to the single heater based on the sensed temperature.

Preferably, the single heater comprises an electric heating element powered by an electric power supply. Where the single heater comprises an electric heating element, the aerosol-generating system and the aerosol-generating device according to the present invention may further comprise an electric power supply and a controller comprising electronic circuitry configured to control the supply of electric power from the electric power supply to the electric heating element. Any suitable electronic circuitry may be used in order to control the supply of power to the electric heating element. The electronic circuitry may be programmable.

The power supply may be a DC voltage source. In preferred embodiments, the power supply is a battery. For example, the power supply may be a Nickel-metal hydride battery, a Nickel cadmium battery, or a Lithium based battery, for example a Lithium-Cobalt, a Lithium-Iron-Phosphate or a Lithium-Polymer battery. The power supply may alternatively be another form of charge storage device such as a capacitor. The power supply may require recharging and may have a capacity that allows for the storage of enough energy for use of the aerosol-generating device with one or more aerosol-generating articles.

Preferably, the single heater is an electric heating element comprising an electrically resistive material. The electric heating element may comprise a non-elastic material, for example a ceramic sintered material, such as alumina ($Al_2O_3$) and silicon nitride ($Si_3N_4$), or printed circuit board or silicon rubber. Alternatively, the electric heating element may comprise an elastic, metallic material, for example an iron alloy or a nickel-chromium alloy.

Other suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium- titanium- zirconium-, hafnium-, niobium-, molybdenum-, tantalum-, tungsten-, tin-, gallium- and manganese- alloys, and super-alloys based on nickel, iron, cobalt, stainless steel, Timetal® and iron-manganese-aluminium based alloys. Timetal® is a registered trade mark of Titanium Metals Corporation, 1999 Broadway Suite 4300, Denver, Colo. In composite materials, the electrically resistive material may optionally be embedded in, encapsulated or coated with an insulating material or vice-versa, depending on the kinetics of energy transfer and the external physicochemical properties required.

The electric heating element may be formed using a metal having a defined relationship between temperature and resistivity. In such embodiments, the metal may be formed as a track between two layers of suitable insulating materials. An electric heating element formed in this manner may be used both as a heater and a temperature sensor.

The single heater may have any shape suitable to heat both the nicotine source and the lactic acid source. In preferred embodiments, the single heater is an elongate internal electric heating element. In particularly preferred embodiments, the single heater is an elongate internal electric heating element having a width that is greater than the thickness thereof so that the elongate internal electric heating element is in the form of a heater blade.

Preferably, the single heater does not project from the aerosol-generating device.

Preferred for use with such an aerosol-generating article is an aerosol-generating device comprising: a body portion comprising the single heater; and a mouthpiece portion configured for engagement with the body portion, wherein the body portion is configured to receive the aerosol-generating article such that the single heater is received in the cavity in the cartridge.

Where the aerosol-generating system according to the present invention comprises an aerosol-generating article comprising the nicotine source and the lactic acid source and an aerosol-generating device comprising the single heater, the aerosol-generating device preferably comprises a cavity configured to receive the aerosol-generating article.

Preferably, the cavity of the aerosol-generating device is substantially cylindrical.

As used herein with reference to the present invention, the terms "cylinder" and "cylindrical" refer to a substantially right circular cylinder with a pair of opposed substantially planar end faces.

Preferably, the cavity of the aerosol-generating device has a diameter substantially equal to or slightly greater than the diameter of the aerosol-generating article.

Preferably, the length of the cavity of the aerosol-generating device is less than the length of the aerosol-generating article so that when the aerosol-generating article is received in the cavity of the aerosol-generating device the proximal or downstream end of the aerosol-generating article projects from the cavity of the aerosol-generating device.

The nicotine source may comprise one or more of nicotine, nicotine base, a nicotine salt, such as nicotine-HCl, nicotine-bitartrate, or nicotine-ditartrate, or a nicotine derivative.

The nicotine source may comprise natural nicotine or synthetic nicotine.

The nicotine source may comprise pure nicotine, a solution of nicotine in an aqueous or non-aqueous solvent or a liquid tobacco extract.

The nicotine source may further comprise an electrolyte forming compound. The electrolyte forming compound may be selected from the group consisting of alkali metal hydroxides, alkali metal oxides, alkali metal salts, alkaline earth metal oxides, alkaline earth metal hydroxides and combinations thereof.

For example, the nicotine source may comprise an electrolyte forming compound selected from the group consisting of potassium hydroxide, sodium hydroxide, lithium oxide, barium oxide, potassium chloride, sodium chloride, sodium carbonate, sodium citrate, ammonium sulfate and combinations thereof In certain embodiments, the nicotine source may comprise an aqueous solution of nicotine, nicotine base, a nicotine salt or a nicotine derivative and an electrolyte forming compound.

Alternatively or in addition, the nicotine source may further comprise other components including, but not limited to, natural flavours, artificial flavours and antioxidants.

The nicotine source may comprise a sorption element and nicotine sorbed on the sorption element.

The sorption element may be formed from any suitable material or combination of materials. For example, the sorption element may comprise one or more of glass, cellulose, ceramic, stainless steel, aluminium, polyethylene (PE), polypropylene, polyethylene terephthalate (PET), poly(cyclohexanedimethylene terephthalate) (PCT), polybutylene terephthalate (PBT), polytetrafluoroethylene (PTFE), expanded polytetrafluoroethylene (ePTFE), and BAREX®.

The sorption element may be a porous sorption element. For example, the sorption element may be a porous sorption element comprising one or more materials selected from the group consisting of porous plastic materials, porous polymer fibres and porous glass fibres.

The sorption element is preferably chemically inert with respect to nicotine.

The sorption element may have any suitable size and shape.

In certain embodiments the sorption element may be a substantially cylindrical plug. For example, the sorption element may be a porous substantially cylindrical plug.

In other embodiments the sorption element may be a substantially cylindrical hollow tube. For example, the sorption element may be a porous substantially cylindrical hollow tube.

The size, shape and composition of the sorption element may be chosen to allow a desired amount of nicotine to be sorbed on the sorption element.

The sorption element advantageously acts as a reservoir for the nicotine.

The lactic acid source may comprise a sorption element and lactic acid sorbed on the sorption element.

The sorption element may be formed from any suitable material or combination of materials, for example those listed above.

The sorption element is preferably chemically inert with respect to lactic acid.

The sorption element may have any suitable size and shape.

In certain embodiments the sorption element may be a substantially cylindrical plug. For example, the sorption element may be a porous substantially cylindrical plug.

In other embodiments the sorption element may be a substantially cylindrical hollow tube. For example, the sorption element may be a porous substantially cylindrical hollow tube.

The size, shape and composition of the sorption element may be chosen to allow a desired amount of lactic acid to be sorbed on the sorption element.

The sorption element advantageously acts as a reservoir for the lactic acid.

Where the aerosol-generating system according to the present invention comprises an aerosol-generating article comprising the nicotine source and the lactic acid source and an aerosol-generating device comprising the single heater, the aerosol-generating article may comprise a first compartment comprising the nicotine source and a second compartment comprising the lactic acid source.

As used herein with reference to the present invention, the term "first compartment" is used to describe one or more chambers or containers within the aerosol-generating article comprising the nicotine source.

As used herein with reference to the present invention, the term "second compartment" is used to describe one or more chambers or containers within the aerosol-generating article comprising the lactic source.

The first compartment and the second compartment may abut one another. Alternatively, the first compartment and the second compartment may be spaced apart from one another.

In use, nicotine vapour is released from the nicotine source in the first compartment and lactic acid is released from lactic acid source in the second compartment. The nicotine vapour reacts with the lactic acid vapour in the gas phase to form an aerosol, which is delivered to a user. Preferably, the aerosol-generating system according to the present invention further comprises a reaction chamber downstream of the first compartment and the second compartment configured to facilitate reaction between the nicotine vapour and the lactic acid vapour. The aerosol-generating article may comprise the reaction chamber. Alternatively, where the aerosol-generating device comprises a body portion and a mouthpiece portion, the mouthpiece portion of the aerosol-generating device may comprise the reaction chamber.

As described further below, the first compartment and the second compartment may be arranged in series or parallel within the aerosol-generating article. Preferably, the first compartment and the second compartment are arranged in parallel.

As used herein, by "series" it is meant that the first compartment and the second compartment are arranged within the aerosol-generating article so that in use an air stream drawn through the aerosol-generating article passes through one of the first compartment and the second compartment and then passes through the other of the first compartment and the second compartment. Nicotine vapour is released from the nicotine source in the first compartment into the air stream drawn through the aerosol-generating article and lactic acid is released from lactic acid source in the second compartment into the air stream drawn through the aerosol-generating article. The nicotine vapour reacts with the lactic acid vapour in the gas phase to form an aerosol, which is delivered to a user.

In certain embodiments the aerosol-generating article may comprise: a housing comprising: an air inlet; a first compartment comprising the nicotine source in communication with the air inlet; a second compartment comprising the lactic acid source in communication with the first compartment; and an air outlet, wherein the air inlet and the air outlet are in communication with each other and configured so that air may pass into the housing through the air inlet, through the housing and out of the housing through the air outlet.

As used herein, the term "air inlet" is used to describe one or more apertures through which air may be drawn into the aerosol-generating article.

As used herein, the term "air outlet" is used to describe one or more aperture through which air may be drawn out of the aerosol-generating article.

In such embodiments, the first compartment and the second compartment are arranged in series from air inlet to air outlet within the housing. That is, the first compartment is downstream of the air inlet, the second compartment is downstream of the first compartment and the air outlet is downstream of the second compartment. In use, a stream of air is drawn into the housing through the air inlet, downstream through the first compartment and then the second compartment and out of the housing through the air outlet.

In such embodiments the aerosol-generating article may further comprise a third compartment in communication with: the second compartment; and the air outlet. In use in such embodiments, a stream of air is drawn into the housing through the air inlet, downstream through the first compartment, the second compartment and then the third compartment and out of the housing through the air outlet.

In such embodiments the aerosol-generating article may further comprise a mouthpiece in communication with: the second compartment or the third compartment, where present; and the air outlet. In use in such embodiments, a stream of air is drawn into the housing through the air inlet, downstream through the first compartment, the second compartment, the third compartment, where present, and then the mouthpiece and out of the housing through the air outlet.

In other embodiments the aerosol-generating article may comprise: a housing comprising: an air inlet; a second compartment comprising the lactic acid source in communication with the air inlet; a first compartment comprising the nicotine source in communication with the second compartment; and an air outlet, wherein the air inlet and the air outlet are in communication with each other and configured so that air may pass into the housing through the air inlet, through the housing and out of the housing through the air outlet.

In such embodiments the second compartment and the first compartment are arranged in series from air inlet to air outlet within the housing. That is, the second compartment is downstream of the air inlet, the first compartment is downstream of the second compartment and the air outlet is downstream of the first compartment. In use, a stream of air is drawn into the housing through the air inlet, downstream through the second compartment and then the first compartment and out of the housing through the air outlet.

In such embodiments the aerosol-generating article may further comprise a third compartment in communication with: the first compartment; and the air outlet. In use in such embodiments, a stream of air is drawn into the housing through the air inlet, downstream through the second compartment, the first compartment and then the third compartment and out of the housing through the air outlet.

In such embodiments the aerosol-generating article may further comprise a mouthpiece in communication with: the first compartment or the third compartment, where present; and the air outlet. In use in such embodiments, a stream of air is drawn into the housing through the air inlet, downstream through the second compartment, the first compartment, the third compartment, where present, and then the mouthpiece and out of the housing through the air outlet.

Where the first compartment and the second compartment are arranged in series within the aerosol-generating article, the second compartment is preferably downstream of the first compartment so that in use an air stream drawn through the aerosol-generating article passes through the first compartment and then passes through the second compartment.

Location of the second compartment comprising the lactic acid source downstream of the first compartment comprising the nicotine source advantageously improves the consistency of the nicotine delivery of the aerosol-generating system. Without being bound by theory, it is believed that location of the lactic acid source downstream of the nicotine source reduces or prevents deposition of lactic acid vapour released from the lactic acid source on the nicotine source during use. This reduces fading over time of the nicotine delivery of the aerosol-generating system. It may also reduce the risk of undesired delivery of unreacted lactic acid vapour to a user.

As used herein, by "parallel" it is meant that the first compartment and the second compartment are arranged within the aerosol-generating article so that in use a first air stream drawn through the aerosol-generating article passes through the first compartment and a second air stream drawn through the aerosol-generating article passes through the second compartment. Nicotine vapour is released from the nicotine source in the first compartment into the first air stream drawn through the aerosol-generating article and lactic acid vapour is released from the lactic acid source in the second compartment into the second air stream drawn through the aerosol-generating article. The nicotine vapour in the first air stream reacts with the lactic acid vapour in the second air stream in the gas phase to form an aerosol, which is delivered to a user.

In certain embodiments the aerosol-generating system comprises: a housing comprising: an air inlet; a first compartment comprising the nicotine source in communication with the air inlet; a second compartment comprising the lactic acid source in communication with the air inlet; and an air outlet, wherein the air inlet and the air outlet are in communication with each other and configured so that air may pass into the housing through the air inlet, through the housing and out of the housing through the air outlet.

In such embodiments the first compartment and the second compartment are arranged in parallel from air inlet to air outlet within the housing. The first compartment and the second compartment are both downstream of the air inlet and upstream of the air outlet. In use, a stream of air is drawn into the housing through the air inlet, a first portion of the stream of air is drawn downstream through the first compartment and a second portion of the stream of air is drawn downstream through the second compartment.

In such embodiments the aerosol-generating article may further comprise a third compartment in communication with: one or both of the first compartment and the second compartment; and the air outlet.

In such embodiments the aerosol-generating article may further comprise a mouthpiece in communication with: the first compartment and the second compartment, or the third compartment, where present; and the air outlet.

In other embodiments the aerosol-generating article comprises: a housing comprising: a first air inlet; a second air inlet; a first compartment comprising the nicotine source in communication with the first air inlet; a second compartment comprising the lactic acid source in communication with the second air inlet; and an air outlet, wherein the first air inlet, the second air inlet and the air outlet are in communication with each other and configured so that air may pass into the housing through the first air inlet, through the housing and out of the housing through the air outlet and air may pass into the housing through the first air inlet, through the housing and out of the housing through the air outlet.

In such embodiments the first compartment and the second compartment are arranged in parallel within the housing. The first compartment is downstream of the first air inlet and upstream of the air outlet and the second compartment is downstream of the second air inlet and upstream of the air outlet. In use, a first stream of air is drawn into the housing through the first air inlet and downstream through the first compartment and a second stream of air is drawn into the housing through the second air inlet and downstream through the second compartment.

In such embodiments the aerosol-generating article may further comprise a third compartment in communication with: one or both of the first compartment and the second compartment; and the air outlet.

In such embodiments the aerosol-generating article may further comprise a mouthpiece in communication with: the first compartment and the second compartment, or the third compartment, where present; and the air outlet.

Where the aerosol-generating article comprises a third compartment, the third compartment may comprise one or more aerosol-modifying agents. For example, the third compartment may comprise one or more sorbents, such as activated carbon, one or more flavourants, such as menthol, or a combination thereof.

Where the aerosol-generating article comprises a mouthpiece, the mouthpiece may comprise a filter. The filter may have a low particulate filtration efficiency or very low particulate filtration efficiency. Alternatively, the mouthpiece may comprise a hollow tube.

One or both of the first compartment comprising the nicotine source and the second compartment comprising the lactic acid source may be sealed by one or more frangible barriers.

The one or more frangible barriers may be formed from any suitable material. For example, the one or more frangible barriers may be formed from a metal foil or film.

In such embodiments the aerosol-generating device preferably further comprises a piercing member configured to rupture the one or more frangible barriers sealing one or both of the first compartment and the second compartment.

Alternatively or in addition, one or both of the first compartment comprising the nicotine source and the second compartment comprising the lactic acid source may be sealed by one or more removable barriers. For example, one or both of the first compartment comprising the nicotine source and the second compartment comprising the lactic acid source may be sealed by one or more peel-off seals.

The one or more removable barriers may be formed from any suitable material. For example, the one or more removable barriers may be formed from a metal foil or film.

In certain preferred embodiments the aerosol-generating article comprises or consists of a cartridge comprising the nicotine source and the lactic acid source.

The cartridge may have any suitable shape.

Preferably, the cartridge is substantially cylindrical.

The cartridge may have any suitable size.

The cartridge may have a length of, for example, between about 5 mm and about 30 mm. In certain embodiments the cartridge may have a length of about 20 mm.

The cartridge may have a diameter of, for example, between about 4 mm and about 10 mm. In certain embodiments the cartridge may have a diameter of about 7 mm.

Preferably, the cartridge comprises a first compartment comprising the nicotine source and a second compartment comprising the lactic acid source.

The cartridge may be formed from one or more suitable materials. Suitable materials include, but are not limited to, aluminium, polyether ether ketone (PEEK), polyimides, such as Kapton®, polyethylene terephthalate (PET), polyethylene (PE), polypropylene (PP), polystyrene (PS), fluorinated ethylene propylene (FEP), polytetrafluoroethylene (PTFE), epoxy resins, polyurethane resins and vinyl resins.

The cartridge may be formed from one or more materials that are nicotine-resistant and lactic acid-resistant.

Alternatively or in addition, the first compartment comprising the nicotine source may be coated with one or more nicotine-resistant materials and the second compartment comprising the lactic acid source may be coated with one or more lactic acid-resistant materials.

Examples of suitable nicotine-resistant materials and lactic acid-resistant materials include, but are not limited to, polyethylene (PE), polypropylene (PP), polystyrene (PS), fluorinated ethylene propylene (FEP), polytetrafluoroethylene (PTFE), epoxy resins, polyurethane resins, vinyl resins and combinations thereof.

Use of one or more nicotine-resistant materials and lactic acid-resistant materials to form the cartridge or coat the interior of the first compartment and the second compartment, respectively, may advantageously enhance the shelf life of the aerosol-generating article.

The cartridge may be formed from one or more thermally conductive materials. Alternatively or in addition, the interior of the first compartment and the second compartment may be coated with one or more thermally conductive materials. Use of one or more thermally conductive materials to form the cartridge or coat the interior of the first compartment and the second compartment advantageously increases heat transfer from the heater to the nicotine source and lactic acid source.

Suitable thermally conductive materials include, but are not limited to, metals such as, for example, aluminium, chromium, copper, gold, iron, nickel and silver, alloys, such as brass and steel and combinations thereof.

Cartridges for use in aerosol-generating systems according to the present invention and aerosol-generating articles according to the present invention may be formed by any suitable method. Suitable methods include, but are not limited to, deep drawing, injection moulding, blistering, blow forming and extrusion.

Preferably, the first compartment and the second compartment are arranged in parallel within the cartridge.

The cartridge may further comprise a third compartment comprising an aerosol-modifying agent. In such embodiments the first compartment, the second compartment and the third compartment are preferably arranged in parallel within the cartridge.

In preferred embodiments the cartridge is substantially cylindrical and the first compartment, the second compartment and, where present, the third compartment extend longitudinally between the opposed substantially planar end faces of the cartridge.

Preferably, the cartridge further comprises a cavity and the aerosol-generating device comprises a single heater configured to be received in the cavity.

In certain preferred embodiments, the aerosol-generating device comprises: a body portion comprising a single heater; and a mouthpiece portion configured for engagement with the body portion, wherein the aerosol-generating device is configured to receive an aerosol-generating article comprising a cartridge comprising a first compartment comprising a nicotine source, a second compartment comprising a lactic acid source and a cavity such that the single heater of the body portion is received in the cavity.

The aerosol-generating article may be received entirely within the body portion of the aerosol-generating device or entirely within the mouthpiece portion of the aerosol-generating device or partially within the body portion of the aerosol-generating device and partially within the mouthpiece portion of the aerosol-generating device.

The aerosol-generating device may further comprise a guide portion configured for engagement with the body portion to facilitate proper alignment of the single heater with the cavity in the cartridge of the aerosol-generating article.

In certain preferred embodiments, the single heater is an internal electric heating element configured to be received in the cavity of the cartridge of the aerosol-generating article. In certain particularly preferred embodiments, the single heater is an elongate internal electric heating element in the form of a heater blade configured to be received in the cavity of the cartridge of the aerosol-generating article. In such embodiments, the cavity in the cartridge of the aerosol-generated article may be configured as an elongate slot.

In preferred embodiments in which the cartridge is substantially cylindrical, the cavity in the cartridge preferably extends along the longitudinal axis of the cartridge between the opposed substantially planar end faces of the cartridge. In such embodiments the first compartment, the second compartment and, where present, the third compartment are preferably disposed around the cavity in the cartridge.

The first compartment may consist of one or more first chambers within the cartridge. The number and dimensions of the first chambers may be chosen to allow a desired amount of nicotine to be included in the cartridge.

The second compartment may consist of one or more second chambers within the cartridge. The number and dimensions of the second chambers may be chosen to allow a desired amount of lactic acid to be included in the cartridge.

The ratio of nicotine to lactic acid in the cartridge required to achieve an appropriate reaction stoichiometry in the gas phase may be controlled and balanced through variation of one or both of the number and dimensions of the one or more first chambers forming the first compartment relative to the number and dimensions of the one or more second chambers forming the second compartment. In other words, the ratio of nicotine to lactic acid in the cartridge required to deliver an appropriate reaction stoichiometry may be controlled through variation of the combined volume of the one or more first chambers (that is, the total volume of the first compartment) relative to the combined volume of the one or more second chambers (that is, the total volume of the second compartment).

In particular, to achieve an appropriate reaction stoichiometry the combined volume of the one or more first chambers forming the first compartment may be less than the combined volume of the one or more second chambers forming the second compartment. For example, the combined volume of the one or more first chambers may be approximately half the combined volume one or more second chambers. That is, the total volume of the first compartment comprising the nicotine source may be approximately half the total volume of the second compartment comprising the lactic acid source.

Alternatively or in addition, the ratio of nicotine to lactic acid required to achieve an appropriate reaction stoichiometry in the gas phase may be controlled and balanced through variation of the volumetric airflow through the one or more first chambers forming the first compartment relative to the volumetric airflow through the one or more second chambers forming the second compartment. The ratio of the volumetric airflow through the one or more first chambers forming the first compartment relative to the volumetric airflow through the one or more second chambers forming the second compartment may be controlled through variation of one or both of the number and dimensions of air inlets in communication with the one or more first chambers relative to the number and dimensions air inlets in communication with the one or more second chambers.

In preferred embodiments in which the cartridge is substantially cylindrical, one or both of the opposed substantially planar end faces of the cartridge may be sealed by one or more frangible barriers.

In such embodiments at least one of the aerosol-generating device and the aerosol-generating article preferably further comprises a piercing member configured to rupture the one or more frangible barriers sealing one or both of the opposed substantially planar end faces of the cartridge.

Alternatively or in addition, one or both of the opposed substantially planar end faces of the cartridge may be sealed by one or more removable barriers. For example, one or both of the opposed substantially planar end faces of the cartridge may be sealed by one or more peel-off seals.

Figure 1:
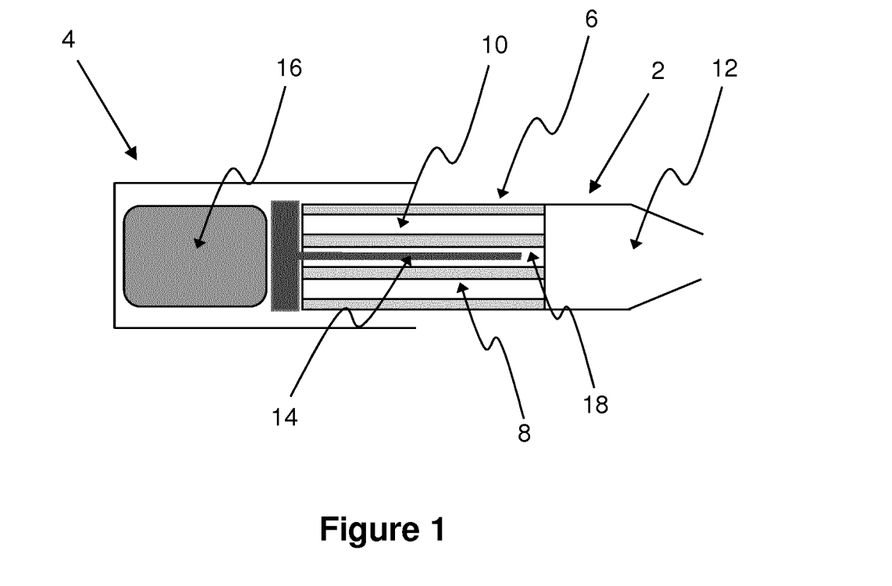
FIG. 1 shows a schematic longitudinal cross-section of an aerosol-generating system according to a first embodiment.

The aerosol-generating system according to the first embodiment of the present invention shown in FIG. 1 generally comprises a first embodiment of an aerosol-generating article 2 according to the present invention and an aerosol-generating device 4, which are configured to engage and cooperate with one another to form the aerosol-generating system.

The aerosol-generating article 2 is configured as a one-piece consumable that is discarded after use. The aerosol-generating article 2 comprises a cartridge 6 comprising a first compartment comprising a nicotine source 8, a second compartment comprising a lactic acid source 10 and a mouthpiece 12. The cartridge may, for example, have a length of about 20 mm and a diameter of about 7.1 mm.

The first compartment comprising the nicotine source 8 and the second compartment comprising the lactic acid source 10 are arranged in parallel within the cartridge 6 at the distal end of the aerosol-generating article 2. The mouthpiece 12 is located downstream of the first compartment comprising the nicotine source 8 and the second compartment comprising the lactic acid source 10 at the proximal end of the aerosol-generating article 2.

Figure 3:
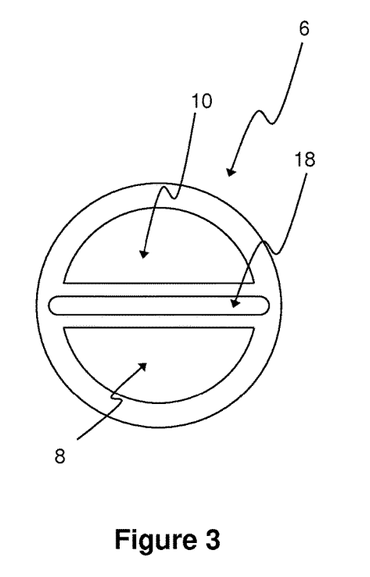
FIG. 3 shows a schematic transverse cross-section of the cartridge of the aerosol-generating articles shown in FIGS. 2a and 2b.

The cartridge 6 of the aerosol-generating article 2 comprises a cavity 18, for example configured as a slot. As shown in FIGS. 1 and 3, the cavity 18 extends along the major axis of the cartridge 6 between the first compartment comprising the nicotine source 8 and the second compartment comprising the lactic acid source 10. The cavity 18 may, for example, have a length of about 15 mm, a width of about 6 mm and a height of about 0.8 mm As shown in FIG. 3, the cartridge 6 comprises two chambers of semi-circular transverse cross-section disposed on either side of the cavity 18. The chambers extend longitudinally between the opposed substantially planar end faces of the cartridge 6. One of the two chambers forms the first compartment comprising the nicotine source 8 and the other of the two chambers forms the second compartment comprising the lactic acid source 10. The distance between the chambers and the cavity 18 may, for example, be about 0.3 mm and the chambers may, for example, have a radius of about 2.6 mm.

The nicotine source 8 comprises a sorption element, such as a PTFE wick, with nicotine adsorbed thereon, which is inserted into the chamber forming the first compartment. The lactic acid source 10 comprises a sorption element, such as a PTFE wick, with lactic acid adsorbed thereon, which is inserted into the chamber forming the second compartment.

The aerosol-generating device 4 comprises a housing comprising a cylindrical cavity in which the cartridge 6 of the aerosol-generating article 2 is received. As shown in FIG. 1, the length of the cavity is less than the length of the aerosol-generating article 2 so that when the cartridge 6 of the aerosol-generating article 2 is inserted into the aerosol-generating device 4 at least the mouthpiece 12 at the proximal end of the aerosol-generating article 2 projects from the cavity.

Figures 2A, 2B:
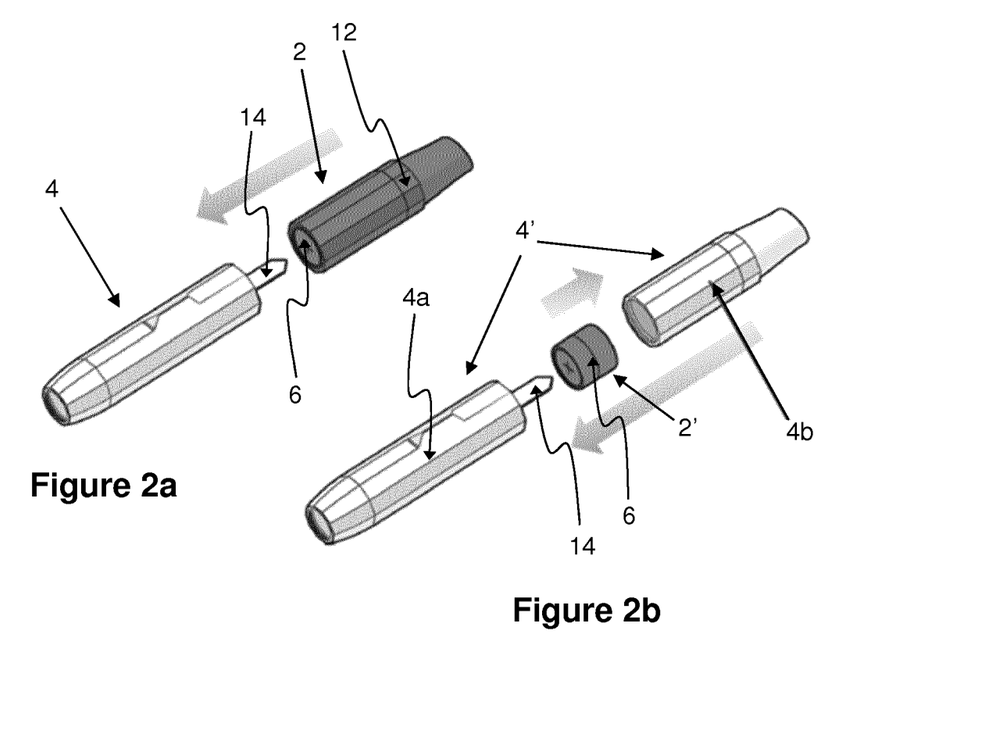
FIG. 2a shows an exploded perspective view of the aerosol-generating system shown in FIG. 1.
FIG. 2b shows an exploded perspective view of an aerosol-generating system according to a second embodiment.

The aerosol-generating device 4 comprises a single heater configured to heat both the nicotine source 8 and the lactic acid source 10 of the aerosol-generating article 2, which is positioned centrally within the cavity of the aerosol-generating device 4 and extends along the major axis of the cavity. The single heater is an elongate electric heating element 14 in the form of a heater blade. As shown in FIG. 2a, the elongate electric heating element 14 projects from the housing of the aerosol-generating device 4. However, in alternative embodiments (not shown), the length of the single heater may be less than the length of the cavity so that the single heater does not project from the housing of the aerosol-generating device 4. The aerosol-generating device 4 further comprises a power supply 16 in the form of a battery and a controller (not shown) comprising electronic circuitry, which is connected to the power supply 16 and the elongate electric heating element 14.

The opposed substantially planar end faces of the cartridge 6 may be sealed by removable barriers, such as peel-off seals (not shown), which may be removed before the cartridge 6 of the aerosol-generating article 2 is inserted into the cavity of the aerosol-generating device 4 to allow a user to draw air though the first compartment comprising the nicotine source 8 and the second compartment comprising the lactic acid source 10 and out of the aerosol-generating article 2 through the mouthpiece 12 at the proximal end thereof.

Alternatively, the opposed substantially planar end faces of the cartridge 6 may be sealed by frangible barriers (not shown). In use, as the cartridge 6 of the aerosol-generating article 2 is inserted into the cavity of the aerosol-generating device 4 one or more piercing members provided in the aerosol-generating device 4 may pierce the frangible barriers to allow a user to draw air though the first compartment comprising the nicotine source 8 and the second compartment comprising the lactic acid source 10 and out of the aerosol-generating article 2 through the mouthpiece 12 at the proximal end thereof.

As shown in FIG. 1, the elongate electrical heating element 14 of the aerosol-generating device 4 is received in the cavity 18 of the cartridge 6 of the aerosol-generating device 4 when the cartridge 6 is inserted into the cavity of the aerosol-generating device 4. The elongate electrical heating element 14 of the aerosol-generating device 4 is thus configured as an internal heater that in use is positioned internally to the aerosol-generating article 2.

Once the cartridge 6 of the aerosol-generating article 2 is inserted into the aerosol-generating device 4, the elongate electric heating element 14 of the aerosol-generating device 4 heats the nicotine source 8 and the lactic acid source 10 in the cartridge 6 to substantially the same temperature of about 100° C.

In use, the user draws on the mouthpiece 12 at the proximal and of the aerosol-generating article 2 to draw air through the first compartment comprising the nicotine source 8 and the second compartment comprising a lactic acid source 10. As the drawn air passes through the cartridge 6, nicotine vapour is released from the nicotine source 8 in the first compartment and lactic acid vapour is released from the lactic acid source in the second compartment. The nicotine vapour reacts with the lactic acid vapour in the gas phase to form an aerosol of nicotine lactate salt particles, which is delivered to the user through the mouthpiece 12 at the proximal end of the aerosol-generating article 2.

The aerosol-generating system according to the second embodiment of the present invention shown in FIG. 2b generally comprises an aerosol-generating article 2' according to a second embodiment of the present invention and an aerosol-generating device 4' according to a first embodiment of the present invention, which are configured to engage and cooperate with one another to form the aerosol-generating system.

The aerosol-generating article 2' comprises a cartridge 6 comprising a first compartment comprising a nicotine source 8 and a second compartment comprising a lactic acid source 10 of identical construction to the cartridge 6 of the aerosol-generating article 2 of the aerosol-generating system according to the first embodiment of the present invention shown in FIGS. 1, 2a and 3. However, unlike the aerosol-generating article 2 of the aerosol-generating system according to the first embodiment of the present invention, the aerosol-generating article 2' of the aerosol-generating system according to the second embodiment of the present invention shown in FIG. 2b does not comprise a mouthpiece.

The aerosol-generating device 4' comprises a body portion 4a comprising a single heater 14 of identical construction to the aerosol-generating device 4 of the aerosol-generating system according to the first embodiment of the present invention shown in FIGS. 1, 2a and 3. However, unlike the aerosol-generating device 4 of the aerosol-generating system according to the first embodiment of the present invention, the aerosol-generating device 4' of the aerosol-generating system according to the second embodiment of the present invention shown in FIG. 2b further comprises a mouthpiece portion 4b configured for engagement with the body portion 4a. As shown in FIG. 2b, the cartridge 6 of the aerosol-generating article 2' is inserted into the aerosol-generating device 4' such that the single heater 14 of the body portion is received in the cavity 18 in the cartridge 6.

In use, the user draws on the mouthpiece portion 4b of the aerosol-generating device 4' to draw air through the cartridge 6 of the aerosol-generating article. As the drawn air passes through the cartridge 6, nicotine vapour is released from the nicotine source 8 in the first compartment and lactic acid vapour is released from the lactic acid source in the second compartment. The nicotine vapour reacts with the lactic acid vapour in the gas phase to form an aerosol of nicotine lactate salt particles, which is delivered to the user through the mouthpiece portion 4b of the aerosol-generating device 4'.

Figure 4:
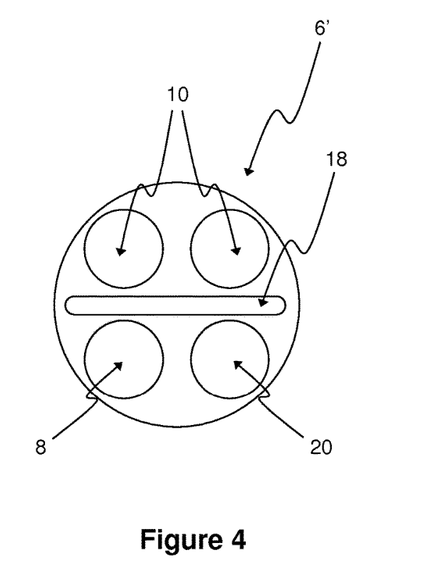
FIG. 4 shows a schematic transverse cross-section of the cartridge of a third embodiment of an aerosol-generating article.

The cartridge 6' of the aerosol-generating article according to the third embodiment of the present invention shown in FIG. 4 is of generally similar construction to the cartridge 6 of the aerosol-generating articles according to the second embodiment of the present invention shown in FIGS. 2b and 3. However, as shown in FIG. 4, the cartridge 6' of the aerosol-generating article according to the third embodiment of the present invention comprises four chambers of substantially circular transverse cross-section, which extend longitudinally between the opposed substantially planar end faces of the cartridge 6'. One of the four chambers forms the first compartment comprising the nicotine source 8 and two of the four chambers form the second compartment comprising the lactic acid source 10. The remaining chamber forms a third compartment comprising a flavour source 20.

The nicotine source 8 comprises a sorption element, such as a PTFE wick, with nicotine adsorbed thereon, which is inserted into the chamber forming the first compartment. The lactic acid source 10 comprises a pair of sorption elements, such as PTFE wicks, with lactic acid adsorbed thereon, which are inserted into the two chambers forming the second compartment. The flavour source 20 comprises a sorption element, such as a PTFE wick, with a flavourant such as menthol adsorbed thereon, which is inserted into the chamber forming the third compartment.

Once the cartridge 6' of the aerosol-generating article 2 is inserted into the aerosol-generating device, the elongate electric heating element 14 of the aerosol-generating device heats the nicotine source 8, the lactic acid source 10 and the flavour source 20 in the cartridge 6' to substantially the same temperature of about 100° C.

In use, the user draws on the mouthpiece portion 4b of the aerosol-generating device 4' to draw air through the cartridge 6' of the aerosol-generating article. As the drawn air passes through the cartridge 6', nicotine vapour is released from the nicotine source 8 in the chamber forming the first compartment, lactic acid vapour is released from the lactic acid source in the two chambers forming the second compartment and flavourant is released from the flavour source in the chamber forming the third compartment. The nicotine vapour reacts with the lactic acid vapour in the gas phase to form an aerosol of nicotine lactate salt particles, which is delivered together with the flavourant to the user through the mouthpiece portion 4b of the aerosol-generating device 4'.

The cartridge 6' may, for example, have a length of about 20 mm and a diameter of about 7.1 mm, the cavity 18 may, for example, have a length of about 15 mm, a width of about 6 mm and a height of about 0.8 mm and the four chambers may have a diameter of about 2 mm.

Figure 5:
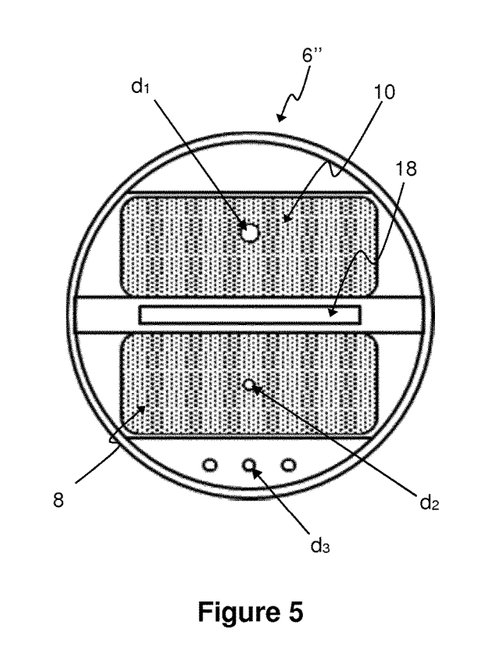
FIG. 5 shows a schematic transverse cross-section of the cartridge of a fourth embodiment of an aerosol-generating article.

The cartridge 6" of the aerosol-generating article according to the fourth embodiment of the present invention shown in FIG. 5 is of generally similar construction to the cartridge 6 of the aerosol-generating article according to the second embodiment of the present invention shown in FIGS. 2b and 3. However, as shown in FIG. 5, the cartridge 6" of the aerosol-generating article according to the fourth embodiment of the present invention comprises a first compartment comprising a nicotine source 8 having an air inlet of diameter $d_2$ and a second compartment comprising a lactic acid source 10 having an air inlet of diameter $d_1$. The diameter $d_2$ of the air inlet of the first compartment controls the volumetric air flow through the first compartment and the diameter $d_1$ of the air inlet of the second compartment controls the volumetric air flow through the second compartment. In use, the reaction stoichiometry of nicotine vapour to lactic acid vapour is controlled and balanced through an appropriate selection of the ratio of the diameter $d_2$ of the air inlet of the first compartment to the diameter $d_1$ of the air inlet of the second compartment.

As shown in FIG. 5, the cartridge 6" of the aerosol-generating article according to the fourth embodiment of the present invention further comprises three ventilation holes of diameter $d_3$. A user may select the level of ventilation (mass dilution) of the aerosol of nicotine lactate salt particles formed by the reaction in the gas phase of the nicotine vapour with the lactic acid by selecting to use, for example, one, two or three of the ventilation holes using a suitable selection mechanism, for example through twisting or rotating of the cartridge 6".

Figure 6:
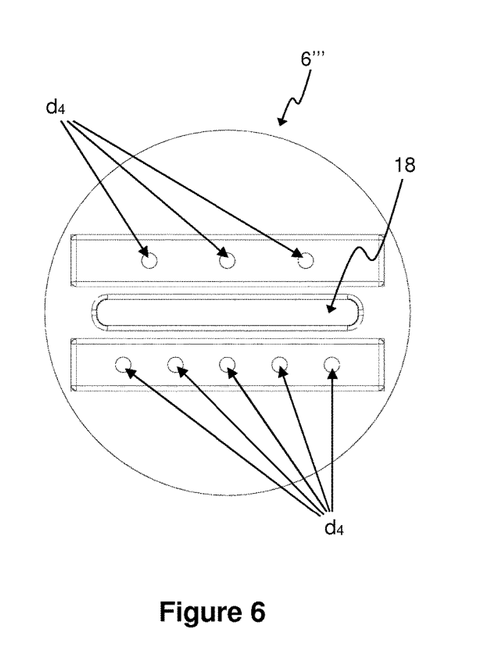
FIG. 6 shows a schematic transverse cross-section of the cartridge of a fifth embodiment of an aerosol-generating article.

The cartridge 6''' of the aerosol-generating article according to the fifth embodiment of the present invention shown in FIG. 6 is of generally similar construction to the cartridge 6" of the aerosol-generating article according to the fourth embodiment of the present invention shown in FIG. 5. However, as shown in FIG. 6, in the cartridge 6''' of the aerosol-generating article according to the fifth embodiment of the present invention comprises a first compartment comprising a nicotine source 8 having a plurality of air inlets of diameter $d_4$ and a second compartment comprising a lactic acid source 10 having a plurality of air inlets of diameter $d_4$. The number of air inlets of diameter $d_4$ for the first compartment controls the volumetric air flow through the first compartment and number of air inlets of diameter $d_4$ for the second compartment controls the volumetric air flow through the second compartment. In use, the reaction stoichiometry of nicotine vapour to lactic acid vapour is controlled and balanced through an appropriate selection of the ratio of the number of air inlets of diameter $d_4$ for the first compartment to the number of air inlets of diameter $d_4$ for the second compartment.

The aerosol-generating system according to the second embodiment of the present invention shown in FIGS. 7(i)-(iii) generally comprises an aerosol-generating article according to the second embodiment of the present invention previously described above and an aerosol-generating device according to a second embodiment of the present invention, which are configured to engage and cooperate with one another to form the aerosol-generating system.

Figure 7:
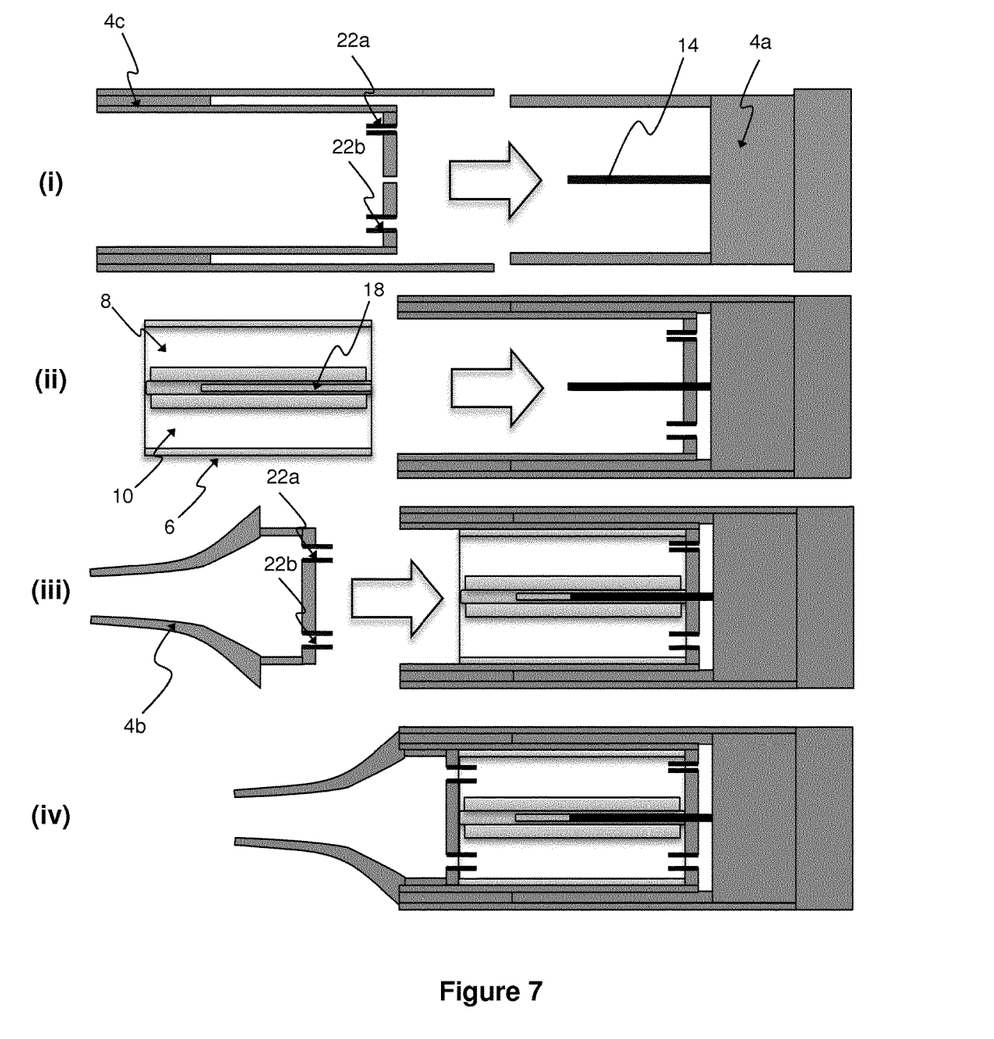

The aerosol-generating device according to the second embodiment of the present invention is of generally similar construction to the aerosol-generating device 4' according to the first embodiment of the present invention shown in FIG. 2b. However, as shown in FIG. 7(i), in addition to a body portion 4a and a mouthpiece portion 4b, the aerosol-generating device 4" according to the second embodiment of the present invention further comprise a guide portion 4c, which is configured for engagement with the body portion 4a. As shown in FIG. 7(ii), the guide portion 4c facilitates proper alignment of the single heater 14 in the body portion 4a of the aerosol-generating device with the cavity 18 in the cartridge 6 of the aerosol-generating article during insertion of the cartridge 6 into the body portion 4a of the aerosol-generating device.

As shown in FIGS. 7(iii) and (iv), the guide portion 4c of the aerosol-generating device according to the second embodiment of the present invention each comprise a pair of piercing element 22a, 22b for piercing frangible barriers sealing the opposed substantially planar end faces of the cartridge 6 to allow air to be drawn through the first compartment comprising the nicotine source 8 and the second compartment of the cartridge comprising the lactic acid source 10, respectively.

The invention has also been exemplified above by reference to an aerosol-generating system comprising an aerosol-generating article comprising a nicotine source and a lactic acid source arranged in parallel within the aerosol-generating article. However, it will be appreciated that in other embodiments the nicotine source and the lactic acid source may be arranged in series within the aerosol-generating system and the aerosol-generating article according to the present invention.

The invention claimed is:

1. An aerosol-generating device, comprising:
a body portion comprising a single heater; and
a mouthpiece portion configured for engagement with the body portion,
the aerosol-generating device being configured to receive an aerosol-generating article comprising a cartridge comprising a first compartment comprising a nicotine source, and a second compartment comprising a lactic acid source and a cavity such that the single heater of the body portion is received in the cavity, wherein the first compartment and the second compartment are arranged in parallel within the cartridge.

2. The aerosol-generating device according to claim 1, wherein the single heater is an elongate internal electric heating element in the form of a heater blade.

3. A method of controlling reaction stoichiometry between nicotine vapour and lactic acid vapour in an aerosol-generating system for the in situ generation of an aerosol comprising nicotine lactate salt particles, the method comprising:
controlling a ratio of a volumetric airflow through a first compartment comprising a nicotine source relative to a volumetric airflow through a second compartment comprising a lactic acid source,
wherein nicotine vapour released from the nicotine source in the first compartment and lactic acid vapour released from the lactic acid source in the second compartment react with one another in a gas phase within the aerosol-generating system to form the aerosol comprising nicotine lactate salt particles, and wherein the first compartment and the second compartment are arranged in parallel within the aerosol-generating system.

4. An aerosol-generating article comprising a cartridge, the cartridge comprising:
a first compartment comprising a nicotine source;
a second compartment comprising a lactic acid source; and
a cavity configured to receive a single heater configured to heat the nicotine source and the lactic acid source, wherein the first compartment and the second compartment are arranged in parallel within the cartridge.

5. The aerosol-generating article according to claim 4, wherein the cartridge further comprises a third compartment comprising an aerosol-modifying agent.

6. The aerosol-generating article according to claim 4, wherein the cartridge is substantially cylindrical and one or both of opposed substantially planar end faces of the cartridge is sealed by one or more frangible or removable barriers.

7. The aerosol-generating article according to claim 4, wherein the first compartment and the second compartment are configured such that a reaction stoichiometry between nicotine vapour and lactic acid vapour is balanced and controlled by a ratio of volumetric air flow through the first compartment relative to volumetric airflow through the second compartment.

8. An aerosol-generating system, comprising:
an aerosol generating article comprising:
a cartridge comprising
a first compartment comprising a nicotine source;
a second compartment comprising a lactic acid source; and
a cavity configured to receive a single heater configured to heat the nicotine source and the lactic acid source, wherein the first compartment and the second compartment are arranged in parallel within the cartridge; and
a separate aerosol generating device comprising the single heater.

9. The aerosol-generating system according to claim 8, wherein the single heater is configured to heat both the nicotine source and the lactic acid source to substantially a same temperature.

10. The aerosol-generating system according to claim 8, wherein the single heater is configured to heat both the nicotine source and the lactic acid source to a temperature of between about 80° C and about 150° C.

11. The aerosol-generating system according to claim 8, wherein the cartridge further comprises a third compartment comprising an aerosol-modifying agent.

12. The aerosol-generating system according to claim 8, wherein the cartridge is substantially cylindrical and one or both of opposed substantially planar end faces of the cartridge is sealed by one or more frangible or removable barriers.

13. The aerosol-generating system according to claim 11, wherein the aerosol-generating device further comprises one or more piercing members configured to rupture the one or more frangible or removable barriers.

14. The aerosol-generating system according to claim 8, wherein the first compartment and the second compartment are configured such that a reaction stoichiometry between nicotine vapour and lactic acid vapour is balanced and controlled by a ratio of volumetric air flow through the first compartment relative to volumetric airflow through the second compartment.

15. The aerosol-generating system according to claim 8, wherein the single heater is an elongate internal electric heating element in the form of a heater blade.

* * * * *